(12) United States Patent
Terada et al.

(10) Patent No.: US 9,486,979 B2
(45) Date of Patent: Nov. 8, 2016

(54) NONWOVEN FABRIC WITH SURFACE UNEVEN STRUCTURE, AND PRODUCT USING SAME

(75) Inventors: Hirokazu Terada, Shiga (JP); Toshikatsu Fujiwara, Shiga (JP)

(73) Assignees: JNC Corporation, Tokyo (JP); JNC Fibers Corporation, Tokyo (JP)

( * ) Notice: Subject to any disclaimer, the term of this patent is extended or adjusted under 35 U.S.C. 154(b) by 529 days.

(21) Appl. No.: 13/379,899

(22) PCT Filed: May 24, 2010

(86) PCT No.: PCT/JP2010/058761
§ 371 (c)(1),
(2), (4) Date: Dec. 21, 2011

(87) PCT Pub. No.: WO2010/150611
PCT Pub. Date: Dec. 29, 2010

(65) Prior Publication Data
US 2012/0107567 A1    May 3, 2012

(30) Foreign Application Priority Data

Jun. 24, 2009  (JP) .................. 2009-149641

(51) Int. Cl.
| | | |
|---|---|---|
| *B32B 3/30* | (2006.01) | |
| *A61F 13/511* | (2006.01) | |
| *D04H 1/541* | (2012.01) | |
| *B32B 5/26* | (2006.01) | |
| *D04H 1/72* | (2012.01) | |

(52) U.S. Cl.
CPC ........... *B32B 3/30* (2013.01); *A61F 13/51104* (2013.01); *B32B 5/26* (2013.01); *D04H 1/541* (2013.01); *D04H 1/72* (2013.01); *Y10T 428/24479* (2015.01)

(58) Field of Classification Search
CPC ......... B32B 5/26; B32B 5/022; B32B 27/12; B32B 37/144; B32B 2305/20; B32B 2250/20; B32B 2262/12; B32B 2432/00; B32B 25/10; B32B 3/20; B32B 15/14; B32B 2307/718; B32B 3/00; B32B 3/30; A47L 13/16; A47L 25/08; D04H 1/5405; D04H 3/14; D04H 5/06; D04H 1/54; D04H 1/542; D04H 1/558; D04H 1/541; Y10T 428/2929
USPC ............... 428/141, 156, 170, 171, 172, 198; 442/361, 362, 363, 364
See application file for complete search history.

(56) References Cited

U.S. PATENT DOCUMENTS

| | | | |
|---|---|---|---|
| 5,198,057 A | 3/1993 | Newkirk et al. | |
| 5,643,653 A * | 7/1997 | Griesbach et al. | ........... 428/120 |

(Continued)

FOREIGN PATENT DOCUMENTS

| | | |
|---|---|---|
| CN | 1662202 | 8/2005 |
| CN | 1715477 | 1/2006 |

(Continued)

OTHER PUBLICATIONS

English Translation of JP 2007-084958; Terada et al.; published Apr. 5, 2007.*

(Continued)

*Primary Examiner* — Catherine A Simone
(74) *Attorney, Agent, or Firm* — Hamre, Schumann, Mueller & Larson, P.C.

(57) ABSTRACT

A nonwoven fabric having a surface concavo-convex structure, and a molded member and a wiping cloth that use the nonwoven fabric are provided. The nonwoven fabric having a surface concavo-convex structure is formed by pressing a planar element having a plurality of apertures against at least one surface of a nonwoven fabric that has been formed by passing hot air through a web including heat adhesive fibers so as to heat-bond interlacing points between the fibers. The pressing process is performed in a state where the nonwoven fabric retains heat in a degree that does not further promote the heat bonding. The nonwoven fabric having a surface concavo-convex structure is soft and exhibits high strength and sufficient resistance against stress.

10 Claims, 2 Drawing Sheets

(56) References Cited

U.S. PATENT DOCUMENTS

| | | | |
|---|---|---|---|
| 5,962,112 A * | 10/1999 | Haynes et al. | 428/198 |
| 6,096,249 A | 8/2000 | Yamaguchi | |
| 2005/0101215 A1 | 5/2005 | Bernstein et al. | |
| 2009/0142595 A1 * | 6/2009 | Matsui | D01F 8/06 428/370 |

FOREIGN PATENT DOCUMENTS

| | | |
|---|---|---|
| JP | 2003-230519 | 8/2003 |
| JP | 2005-350836 | 12/2005 |
| JP | 2006-045724 | 2/2006 |
| JP | 2007-084958 | 4/2007 |
| JP | 2007-510816 | 4/2007 |
| TW | 387954 | 4/2000 |
| WO | 98/27257 | 6/1998 |
| WO | WO 2007066599 A1 * | 6/2007 ............... D01F 8/06 |

OTHER PUBLICATIONS

Ma, et al., "Introduction to the technique of Non-Woven Fabrices (Second Edition)", China Textile & Apparel Press, version 2, p. 73, Aug. 31, 2008—partial English translation.

* cited by examiner

NONWOVEN FABRIC WITH SURFACE UNEVEN STRUCTURE, AND PRODUCT USING SAME

TECHNICAL FIELD

The present invention relates to a nonwoven fabric having a concavo-convex surface structure and a product using the same. More specifically, the present invention provides a nonwoven fabric with an appearance having bulky hill parts filled with fibers and less bulky plain parts, where the bill parts and the plain parts are intermingled on the surface. The present invention further provides a nonwoven fabric whose appearance provided with a concavo-convex surface can be changed arbitrarily depending on the application, and also provides a fiber product using the same.

BACKGROUND ART

For a method of producing a concavo-convex nonwoven fabric, a heat-compressed nonwoven fabric formed by using an embossing roll is widely known. However, since such a nonwoven fabric is formed by heat compression, the bulk of the thus obtained concavo-convex nonwoven fabric is rather low. The compressed part becomes like a film, and the feeling of the thus obtained nonwoven fabric deteriorates. Even the remaining parts other than the heat compressed part easily lose the bulkiness under the influence of the heat compressing action.

An example of methods for increasing the bulkiness is implied by a floor-cleaning sheet (see Patent document 1), which is produced by laminating a fibrous web based on a heat-adhesive fiber and a mesh sheet as a supporter, through which hot air is passed so as to integrate the fibrous web and the mesh sheet thereby forming concaves and convexes.

However, when the region of the fibrous web for passing the hot air is decreased due to the use of the mesh sheet, turbulence occurs in the hot air in a region where the hot air does not pass through. This causes some problems, for example, the accumulation of fibers in the web is disordered. Adhesiveness is degraded at parts not passing the hot air, and the nonwoven fabric strength deteriorates. Thus the shape of the concave-convex and the area of the concaves are restricted.

In an alternative method disclosed for forming a concavo-convex nonwoven fabric, a nonwoven fabric is prepared by partially heat-compressing to join two layers by use of a heat-embossing roll, where the first layer containing heat shrinkable fibers has a maximal heat-shrinkage developing temperature that is lower than the melting point of a second layer made of non-heat shrinkable fibers, and by heating the nonwoven fabric to shrink the heat shrinkable layer so as to form the concavo-convex nonwoven fabric (see Patent document 2).

In this case, the concave parts become film-like to some extent, and thus the air permeability and the feeling deteriorate when the concave area is increased. The feeling becomes rigid when the temperature at the heating for shrinkage is higher than the melting point of the unshrinkable fiber. On the other hand, when the temperature in heating is equal or lower than the melting point of the unshrinkable fibers, the feeling is improved, but problems occur, for example, the sufficient strength cannot be obtained, and the dimensional stability of the obtained nonwoven fabric is not satisfactory. Since the convex parts have a lot of voids, the resistance against stress is inherently insufficient.

PRIOR ART DOCUMENTS

Patent Documents

Patent document 1: JP 2003-230519 A
Patent document 2: JP 2006-45724 A

DISCLOSURE OF INVENTION

Problem to be Solved by the Invention

For solving the above-mentioned problems, an object of the present invention is to provide a nonwoven fabric having a surface concavo-convex structure that can be formed to have an arbitrarily concavo-convex shape (providing concavo-convex shape), exhibits softness and high strength, and has sufficient resistance against stress. Another object of the present invention is to provide such a nonwoven fabric at a low cost.

Means for Solving Problem

The inventors of the present invention have made earnest studies so as to solve the above-described problems. As a result, they found that the problems can be solved by a product that is obtained by pressing an element having a plurality of apertures against at least one surface of a nonwoven fabric where the interlacing points between fibers have been heat bonded by passing hot air through, and subsequently by removing the element, and the inventors have completed the present invention on the basis of this finding.

The present invention has the following configurations.
(1) A nonwoven fabric having a surface concavo-convex structure, formed by pressing a planar element having a plurality of apertures against at least one surface of a nonwoven fabric that has been prepared by passing hot air through a web including heat adhesive fibers so as to heat-bond interlacing points between the fibers,
the pressing process is performed in a state in which the nonwoven fabric retains heat in a degree that does not further promote the heat bond.
(2) The nonwoven fabric according to the above (1), wherein the heat adhesive fibers are heat adhesive conjugated fibers.
(3) The nonwoven fabric according to the above (1) or (2), wherein the planar element having a plurality of apertures is a cylindrical roll that is used as a rotational roll through which the nonwoven fabric is passed while being pressed against the rotational roll, where the nonwoven fabric has been prepared by passing hot air through the web including heat adhesive fibers so as to heat-bond the interlacing points between the fibers.
(4) The nonwoven fabric according to any of the above (1) to (3), wherein the web is a laminate.
(5) The nonwoven fabric according to any of the above (1) to (4), having a weight per unit (metsuke) of 15 to 60 $g/mm^2$ and a maximal thickness in the range of 0.2 to 5 mm.
(6) The nonwoven fabric according to any of the above (1) to (5), wherein the difference in the height between a convex part and an adjacent concave part on at least one surface is in a range of 0.1 to 4.5 mm.

(7) A molded member obtained by integrating the nonwoven fabric according to any of the above (1) to (6) with an additional layer.
(8) A product obtained by use of the nonwoven fabric according to any of the above (1) to (6) or the molded member according to the above (7).
(9) A wiping cloth obtained by use of the nonwoven fabric according to any of the above (1) to (6) or the molded member according to the above (7).

Effects of the Invention

The nonwoven fabric having a concavo-convex surface structure according to the present invention has particularly bulky bill parts (corresponding to convexes) and less bulky plain parts (corresponding to concaves) that are intermingled, and thus it has bulkiness, and excellent softness and strength. Furthermore, it has favorable air permeability, and can be produced at a low cost.

BRIEF DESCRIPTION OF DRAWINGS

FIG. 2 includes diagrams showing an example of a molded member of the present invention integrated with a web layer of polyester fibers as an additional layer.
FIG. 3 includes diagrams showing an example of a sanitary napkin as a product of the present invention using the molded member as shown in FIG. 2.

DESCRIPTION OF THE INVENTION

Figure 1:
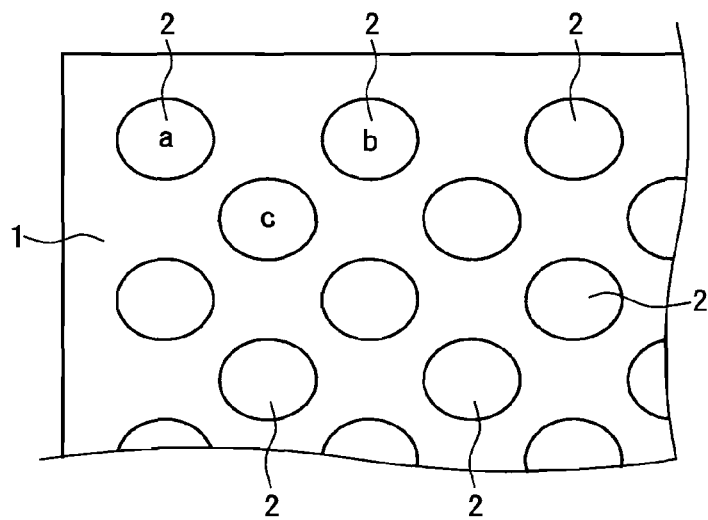
FIG. 1 is a partial plan view showing an example of a planar element having a plurality of apertures used in the present invention.

A concavo-convex nonwoven fabric of the present invention is a nonwoven fabric characterized in that bulky hill parts (corresponding to convexes) and less bulky plain parts (corresponding to concaves) are intermingled on the surface of the nonwoven fabric including heat adhesive fibers.

Specifically, it is a nonwoven fabric having a concavo-convex surface structure obtained by pressing a planar element having a plurality of apertures against a nonwoven fabric prepared by passing hot air through a web including heat adhesive fibers, in a state where the nonwoven fabric retains heat in a degree that does not further promote the heat adhesive of the nonwoven fabric.

An example of the heat adhesive fibers is a conjugated fiber having a heat adhesive characteristic. The heat adhesive component of the heat adhesive fiber is not limited particularly as long as it is a thermoplastic resin component that melts due to heat when hot air is passed through a web of the fibers, thereby forming bonding points. In the present invention, the heat bonding points between fibers are formed as a result of melting a thermoplastic resin component having a low melting point with the hot air treatment. Examples of the resin components for forming the heat adhesive fibers include polyolefin-based resin (for example, polypropylene, a propylene copolymer [which is a copolymer of propylene as main component and another α-olefin; the examples include an ethylene-propylene binary copolymer, a propylene-butene-1 binary copolymer, and a propylene-hexene-1 binary copolymer], and polyethylene), polyester-based resin (for example, polyethylene terephthalate), and polyamide-based resin (for example, nylon-6). Specific examples of combinations of a low-melting point component and a high-melting point component in a conjugated fiber include a combination of polyethylene (low-melting point component) and polypropylene (high-melting point component), and a combination of polyethylene (low-melting point component) and polyethylene terephthalate (high-melting point component) etc. From the viewpoint of bulkiness and nonwoven fabric strength, a conjugated fiber of polyethylene and polyethylene terephthalate is preferred in particular. Examples of the conjugated fiber shape in the cross section perpendicular to the longitudinal direction include a concentric core-sheath type, an eccentric core-sheath type, a parallel type, a radial type and the like. From the viewpoint of bulkiness, an eccentric core-sheath type is preferred in particular. In the case of the concentric core-sheath type or the eccentric core-sheath type conjugated fiber, the low-melting point component forms the sheath component, and the high-melting point component forms the core component.

The respective melting points of the low-melting point component and the high-melting point component in the conjugated fiber can be measured by differential scanning calorimetry.

Though the fineness of the heat adhesive fiber is not limited particularly, a small fineness will be selected when the feeling is valued highly, and the range is 0.5 dtex to 4 dtex, preferably 1 dtex to 3 dtex.

It is characteristic in particular that a bulky web can be used in producing the nonwoven fabric of the present invention. In a conventional method (the method as recited in the above Patent document 2), a shrinkable fiber layer and an unshrinkable fiber layer are partially joined and laminated, and the unshrinkable fiber layer is allowed to protrude in the regions between the partial joints so as to develop a concavo-convex shape in the fiber sheet by use of the shrinkage of the shrinkable fiber layer. In the method, when the unshrinkable fiber layer in use is bulky, a great stress is required to make it protrude (i.e., to warp the unshrinkable fiber layer), and thus in some cases a sufficient concavo-convex shape cannot be formed. In a forcible formation of the concavo-convex shape, accompanied with the heat applied at the time of heat shrinkage, the partial joints to integrate the both layers may be destroyed as they cannot stand the stress caused by the protrusion and warping. Thereby the layers may be peeled off.

In a method of forming convexes and concaves with a conventional heat embossing roll (an embossing roll denotes an apparatus provided with a roll having convex-concave pattern formed on the surface, which can compress and bond a web with heat by use of a combination of the embossing roll and a flat roll, or a combination of an embossing roll and another embossing roll), when a bulky web is used, it is necessary to engrave the embossing roll to have a deeply embossed pattern with a great difference in height between a convex and a concave. In particular, when the distance between pitches of the convexes is relatively long, even if the concaves are engraved deep, the web will contact the concaves of the embossing roll. From the viewpoint of the cost for the engraving, use of a bulky web will have various limitations in this method.

When a heat embossing roll is used, the convexes of the embossing roll are transcribed to the nonwoven fabric so as to form a compressed part. In this case, for obtaining a high nonwoven fabric strength, it is required to increase the area of the compressed part. Since the heat embossed part becomes like a film due to heat compression and the voids of the entire nonwoven fabric are decreased, the feeling and the air permeability deteriorate considerably, namely, it is difficult to balance the strength with the feeling.

However, in the present invention, the convexes formed on the nonwoven fabric surface are not pressed against the planar element base at the apertures of the planar element having apertures. Therefore, during a process of forming the convexes, the sites are free toward the upper space in the thickness direction of the nonwoven fabric (i.e., the sites are not suppressed to decrease its bulk). As a result, even when the web in use is particularly bulky, there is no difficulty in production of a nonwoven fabric having a concavo-convex surface structure. In the present invention, the term "apertures" in a planar element having apertures denotes through holes in the direction from the surface to back face of the planar element. Although the sites where the convexes are formed are free toward the upper space, since the heat adhesive conjugated fibers forming this site have been heat-bonded at the interlacing points, even in the process of forming the convex parts, the integrity as the fiber layer will not be sacrificed particularly at the convex parts. Shedding of fibers or fluffing will not occur at the sites. Similarly at the concave parts, although compressed parts are formed as a result of pressing the planar element, since the process of pressing the planar element is performed in a state where the nonwoven fabric retains heat in a degree that does not further promote the heat bonding, a heat-compressed structure is not provided unlike the case of using a heat embossing roll, and thus even the compressed part can maintain a comparatively high percentage of voids. Furthermore, regardless of heating of the embossing roll, in a product formed by pressing with an embossing roll, the compressed parts are scattered. In contrast, the compressed parts according to the present invention surround the convex parts and form a network linked on the nonwoven fabric surface. Due to this structure, even though the strength at a compressed part formed between a pair of convex parts adjacent to each other is poorer than that at a compressed part formed by using an embossing roll, the nonwoven fabric as a whole can have excellent strength. Since appropriate voids are retained, the feeling and the air permeability are not sacrificed while a high strength is exhibited.

From the viewpoint of clarifying the convex parts of the nonwoven fabric, it is preferable that the weight per unit of the web in use is in a range of 15 to 60 g/m$^2$, and it is particularly preferable that the weight per unit is in a range of 20 to 35 g/m$^2$. From the viewpoint of the bulkiness, it is preferable that the apparent specific volume is in a range of 20 to 70 cm$^3$/g, and it is particularly preferable that the apparent specific volume is in a range of 25 to 60 cm$^3$/g.

In the web used in the present invention, fibers other than a so-called heat adhesive fibers (hereinafter, referred to as "non-heat adhesive fibers") may be blended. Examples of the non-heat adhesive fibers include natural fibers (wood fibers and the like), regenerated fibers (rayon and the like), semi-synthetic fibers (acetate and the like), chemical fibers and synthetic fibers (polyester, acrylic, nylon, vinyl chloride and the like). The term "non-heat adhesive fibers" in the present invention denotes fibers that do not cause a thermal conversion (melting or softening) relating to heat adhesion under a condition of hot air treatment when the blended non-heat adhesive fibers are subjected to the hot air treatment together with the heat adhesive fibers. Therefore, these fibers may be regular fibers (single fibers) or conjugated fibers as long as the above conditions are met.

Though it is difficult to define the blend ratio of the non-heat adhesive fibers since the ratio varies depending on the types of the fibers in use and/or the desired performance of the nonwoven fabric, the ratio of these non-heat adhesive fibers is 5 to 90 wt %, or more preferably 10 to 60 wt % with regard to the total weight of the web. The web used in the present invention may be a laminate including any other layers that can permeate hot air as long as the desired effects of the present invention including the convex-concave formation and processability are not inhibited. The examples include fiber layers (e.g., fibrous web, nonwoven fabric, woven fabric and knitted fabric), a punched sheet and a porous film. The layer for lamination has a melting point higher than the temperature of the hot air. Bonding with the other layer may be performed by any techniques such as an air-through method, a needle-punching method, a waterstream interlacing method, heat compression, adhesion with an adhesive, and adhesion using a hot-melt adhesive, as long as the features of the nonwoven fabric having the surface concavo-convex structure according to the present invention are not sacrificed excessively. In general, lamination using a hot-melt adhesive is preferred.

For producing a nonwoven fabric where the interlacing points between fibers are heat-bonded by passing hot air through a web including the heat adhesive fibers, for example, an ordinary hot air processor (suction band dryer) can be used for the purpose of hot air treatment under an ordinary condition. In general, a hot air processor is used to blow hot air at a certain temperature to a web fed onto an automotive conveyer net and at the same time to draw the hot air passing through the web from the bottom of the conveyer net. The processor is suitable for processing the heat adhesive conjugated fibers so as to make a bulky nonwoven fabric.

The temperature of the hot air is not limited in particular as long as the heat adhesive fibers bond sufficiently to each other by heat at the interlacing points. Preferably, the hot air treatment is performed at a temperature higher by a range of 1 to 10° C. than the melting point of the resin components of the heat adhesive fibers. From the viewpoint of bulkiness, it is preferable to perform the hot air treatment at a temperature higher by a range of 1 to 5° C. than the melting point of the low-melting point resin component and lower by a range of 10 to 30° C. than the melting point of the high-melting point resin component. Therefore, a conjugated fiber where the difference in the melting points between the low-melting point resin component and the high-melting point resin component is 11 to 35° C. is used preferably.

A planar element having a plurality of apertures is pressed against at least one surface of the nonwoven fabric where the interlacing points between fibers have been heat-bonded by hot air, and subsequently, the planar element is removed to obtain a nonwoven fabric having a surface concavo-convex structure. Though it is also possible to provide the concavo-convex shape by pressing a flat plate having a plurality of apertures, from the viewpoint of workability, it is preferable that the concavo-convex shape is provided to the nonwoven fabric where the interlacing points between the fibers have been heat bonded, by pressing the nonwoven fabric through at least one rotational roll having on its surface a plurality of apertures. The time for pressing is not limited particularly as long as the concavo-convex shape is provided sufficiently. In a case of using a rotational roll having a plurality of apertures on the surface. The rotational rate of the roll can be set to a range of 1 to 100 m/min., although the rate is not limited to this example in particular. In an example of the method, a nonwoven fabric where the interlacing points between the fibers of web have been heat-bonded is prepared by using a hot air circulation heat processor. Subsequently, a rotational roll having a plurality of apertures on the surface is set on a conveyer placed next (exit) to the processor, so that the nonwoven fabric is passed between the conveyer and the rotational roll having a plurality of apertures on the surface. Thereby, the pattern of the apertures of the roll is transcribed on the nonwoven fabric and the concavo-convex structure is formed on the nonwoven fabric.

The pressure for pressing the planar element having a plurality of apertures against the nonwoven fabric can be selected arbitrarily as long as the pressure is sufficient to form the concavo-convex shape and to prevent excess compression of the concaves, taking the shape and the nature of the nonwoven fabric into consideration. A preferred range is 0.098 MPa to 2.0 MPa. A range of 0.2 MPa to 1.0 MPa is preferred further from the viewpoint of preventing excessive compression of the concaves. This holds true for a roll-type planar element. It is also possible to use a flat plate in place of the roll as the planar element. Alternatively, a curved plate may be used as a planar element so that the object of the present invention can be achieved easily. When a roll-like planar element is used as a rotational roll, the roll may have rod-like supportive members at both ends in the longitudinal direction of the roll, and the supportive members extend from the rotational bearing at the center of the roll cross section radially in the roll's plane just like a spoke of a bicycle. An alternative roll may have a disk having at the center a hole for bearing, and the disk is implanted at the both ends in the longitudinal direction of the roll. Needless to note, in such a case, the rod-like supportive member or the disk will be arranged at a position so as not to block the apertures formed on the roll curved surface from the interior of the roll. Normally, the length of the roll is set to be longer than the width of the nonwoven fabric whose interlacing points have been heat-bonded, so that the rod-like supportive member or the disk will be provided outside the width of the nonwoven fabric. However, the present invention is not limited to this example.

In the pressing process with the planar element having a plurality of apertures, it is preferable that a melt other than the heat bonding in the previous step of hot air treatment does not occur in the nonwoven fabric. On the other hand, care should be taken such that the concave structure compressed by the pressing process does not recover its original unpressed state. For this purpose, in the pressing process, it is preferable that the nonwoven fabric is heated to a degree that avoids the heat melting, namely, to a degree that does not promote the further heat bonding in the nonwoven fabric. It is not necessary that the planar element having a plurality of apertures be heated during the pressing process. However, it is preferable that the pressing process is performed while the heat applied in the preceding hot air treatment remains in the nonwoven fabric. In a case of heating a planar element having a plurality of apertures (in a case where sufficient heat is not retained in the nonwoven fabric or in a case where the pressing process is performed after the nonwoven fabric is cooled down), the planar element may be heated during the pressing process to a temperature not to cause heat melt in the fibers of the nonwoven fabric. In such a case, it is preferable that the temperature of the nonwoven fabric is 50° C. or higher and lower by at least 5° C. than the melting point of the heat adhesive fiber (or the melting point of the low-melting point component of a conjugated fiber). Further, for a temperature for preventing excessive compression of the concaves, a temperature of 60° C. or higher and lower by at least 10° C. than the melting point of the heat adhesive fiber is preferred. It is particularly preferable that the temperature is 70° C. or higher and lower by at least 20° C. than the melting point of the heat adhesive fiber. When the temperature of the warmed nonwoven fabric is lower by at least 5° C. than the melting point of the heat adhesive fiber, the less bulky plain parts will not become like a film. When the temperature is 50° C. or higher, the less bulky plain parts will not recover its original unpressed state, and thus the clear concavo-convex structure can be maintained. In this context, "the planar element is heated" includes a state where the heat remaining in the web is conducted to the planar element during the process of pressing to the web, and as a result, the planar element retains heat sufficient to provide the concavo-convex structure to the nonwoven fabric.

Therefore, in the present invention, "(be) performed in a state . . . retains heat" in the context of "the pressing process is performed in a state where the nonwoven fabric retains heat in a degree that does not promote further heat bonding in the nonwoven fabric" indicates that the nonwoven fabric itself is maintained at the above-mentioned temperature. Alternatively, the planar element itself has been heated so that the heat remaining in the web is conducted to the planar element during the process of pressing the web, and as a result, the pressing process is performed in a state where the planar element retain heat sufficient to provide the concavo-convex structure to the nonwoven fabric.

The planar element for the pressing process is not limited in particular as long as it has apertures, for example. It is not limited to the roll as mentioned above, but can be a plate (a flat plate or a curved plate). The planar element may be arranged at the exit of the hot air processor or may be arranged during any of the following process steps. It is preferable that the temperature of the nonwoven fabric at the time of pressing the nonwoven fabric with the planar element is in the above-mentioned range From the viewpoint of energy efficiency, it is preferable that the planar element is not heated affirmatively, but hot air is passed through the web at the time of heat bonding the interlacing points of the fibers and the heat applied to the nonwoven fabric at that time is used for the pressing process. In this case, the distance from the exit of the hot air processor to the entrance of the presser (planar element) is set to maintain the temperature of the nonwoven fabric.

In the planar element having a plurality of apertures, the shape of each aperture may be varied, for example, a circle, a square, a hexagon, an ellipse, a rectangle, a rhombus, a cross and the like, without any particular limitations. The dimension of one aperture is preferably in a range of 7 to 150 mm$^2$, and the arrangement can be selected arbitrarily for example, a parallel arrangement, a staggered arrangement, an irregular arrangement and the like. From the viewpoint of the nonwoven fabric strength, the staggered arrangement is preferred.

FIG. 1 is a partial plan view showing an example of a planar element having a plurality of apertures used in the present invention. A planar element 1 in FIG. 1 has circular apertures 2. A staggered arrangement of the apertures denotes a pattern as shown in FIG. 1 where the apertures a, b, and c are formed to define apices of a substantially equilateral triangle, and the equilateral triangle is repeated at a constant pitch. However, the present invention is not limited to this example.

Regarding a planar element having a plurality of apertures, the apertures make bulky hill parts (convexes) in the obtained nonwoven fabric having a concavo-convex surface structure, and the continuous plane between the apertures makes a less bulky plain part (concave). It is preferable that the porosity of the apertures in the planar element at the site to get contact with the nonwoven fabric is in a range of 10 to 90%, and more preferably, in a range of 20 to 80%. The surface area of the less bulky plain part may be decreased to obtain a softer nonwoven fabric, and the porosity can be varied arbitrarily in accordance with the application and the object.

The material of the planar element is not limited in particular as long as it can stand the loads such as heating and pressure provided by the pressing or the like as mentioned above. The examples include stainless steel (SUS) and aluminum. From the viewpoint of heat resistance and pressure resistance, SUS is used preferably. There are not any particular limitations on the thickness and dimension of the planar element.

The weight per unit of the nonwoven fabric having the surface concavo-convex structure is preferably in a range of 15 $g/m^2$ to 60 $g/m^2$. More preferably, it is 15 $g/m^2$ to 50 $g/m^2$, and further preferably, 15 $g/m^2$ to 30 $g/m^2$.

Further, the thickness of the nonwoven fabric having the surface concavo-convex structure is not limited particularly. It is preferable that the thickness at the thickest sites (convexes) is in a range of 0.2 to 5 mm. It is further preferable that the difference in height between a convex on at least one surface and the adjacent concave is in a range of 0.1 to 4.5 mm. The means for providing a surface concavo-convex structure to a nonwoven fabric in the present invention is characterized in particular in its excellent feature of providing a concavo-convex shape to a bulky web. As a result, a nonwoven fabric that is relatively thick and bulky and that has a large difference between the convexes and concaves can be obtained in an efficient manner.

It is also possible to laminate a fiber layer, a sheet, a film and the like on the nonwoven fabric having the surface concavo-convex structure, and integrate to form a molded member as long as the effect of the present invention is not affected. The fiber layer (fibrous web, nonwoven fabric, woven fabric, knitted fabric and the like) includes wood fibers such as cotton and linen, natural fibers, chemical fibers such as rayon and acetate, and synthetic fibers such as polyolefin, polyester, acrylic, nylon, vinyl chloride and the like. In this case, the additional layer may be integrated with the concavo-convex surface of the nonwoven fabric having the surface concavo-convex structure, or may be integrated with the other surface. The processes for integration include an air-through method, a needle-punching method, a water-stream interlacing method and a hot melt bonding method that uses a hot-melt adhesive, though the present invention is not limited to these examples.

For example, by laminating a web of polyester fibers with the concavo-convex nonwoven fabric and integrating, some effects are obtained, for example, a molded member with high cushioning properties can be obtained.

The product using the molded member can be used for hygienic goods and industrial materials. For example, for a hygienic good, the product is used as a top sheet of a sanitary napkin or a surface material of a disposable diaper so that the concavo-convex part will make the surface in contact with skin. As a result, appropriate spacing can be held between the nonwoven fabric and the skin, and possibly rash caused by menstrual blood or urine can be prevented. When the product is applied to industrial materials to make packing materials and soundproof sheets, cushioning effects or sound-absorbing effects due to the convexes and the concaves can be expected.

Furthermore, due to the scraping effect (scraping at the convexes and collecting at the concaves) provided by the concavo-convex parts, the product may be used preferably as a wiping cloth. Therefore, when the product is laminated with any other members, for example, when the product is arranged so that the convexes and the concaves on a top sheet of a sanitary napkin or a surface material of a disposable diaper will be in contact with the skin, or when the product is used as a wiping cloth member for its scraping effect of the convexes and the concaves, the other member will be laminated on the surface of the nonwoven fabric opposite to the surface on which the convexes and the concaves have been formed. In a case where the convexes and the concaves in the nonwoven fabric of the present invention are formed on the both surface of the nonwoven fabric, the additional member will be laminated on any one of the surfaces. Needless to note, the nonwoven fabric of the present invention may be used as a wiping cloth without laminating any other members.

Figure 2A:
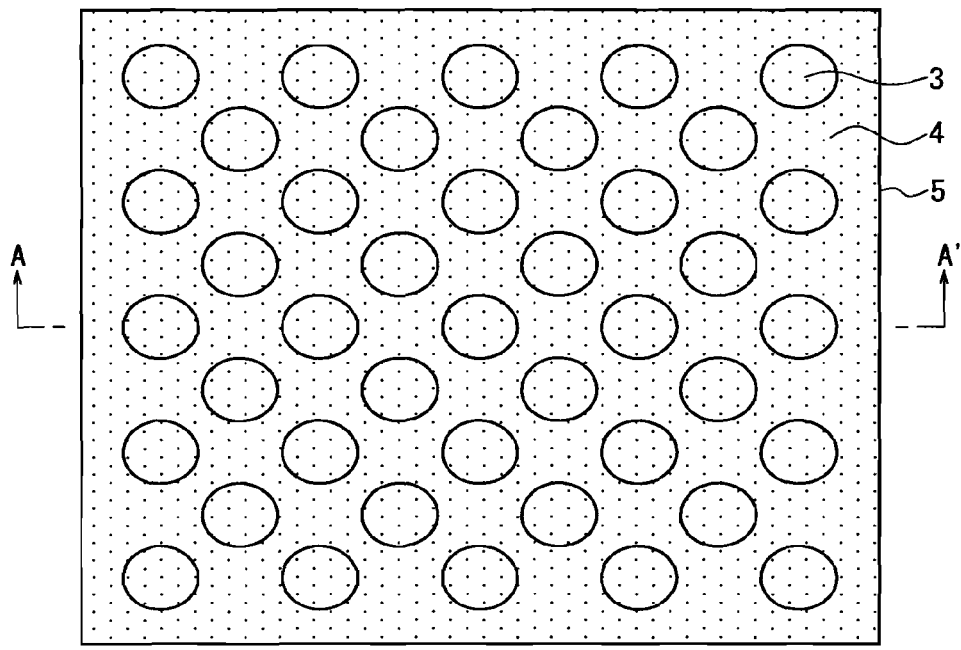
FIG. 2A is a plan view showing the molded member from the nonwoven fabric side having the surface concavo-convex structure of the present invention.
Figure 2B:
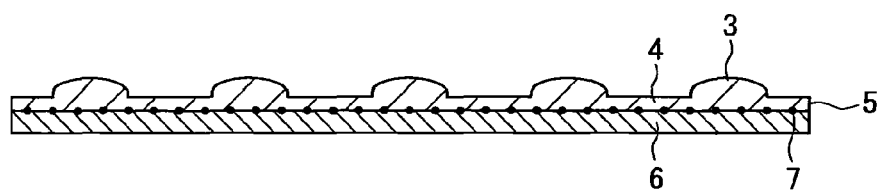
FIG. 2B is a cross-sectional view taken along a line A-A' in FIG. 2A.

FIG. 2 shows an example of a molded member obtained by laminating an additional layer on the nonwoven fabric of the present invention. FIG. 2A is a plan view showing the member from the nonwoven fabric side having the surface concavo-convex structure of the present invention, and FIG. 2B is a cross sectional view taken along the line A-A' in FIG. 2A.

The molded member as shown in FIG. 2 is obtained by integrating a nonwoven fabric 5 having the surface concavo-convex structure according to the present invention and a web layer 6 of polyester fibers by use of a hot melt adhesive 7 or the like. The cushioning properties provided by the lower layer of polyester fibers are conducted to the surface concavo-convex structure on the upper layer. For example, when the nonwoven fabric is used as a wiping cloth, the scraping effect is improved due to the cushioning properties. When it is used as a surface material of sanitary goods such as sanitary napkins, the appropriate skin contact due to the surface concavo-convex structure serves to prevent rash and the lower layer provides cushioning properties to improve the feeling. Numeral 3 denotes convexes parts) and 4 denotes a concave (plain part) of a nonwoven fabric having the surface concavo-convex structure of the present invention.

Figure 3A:
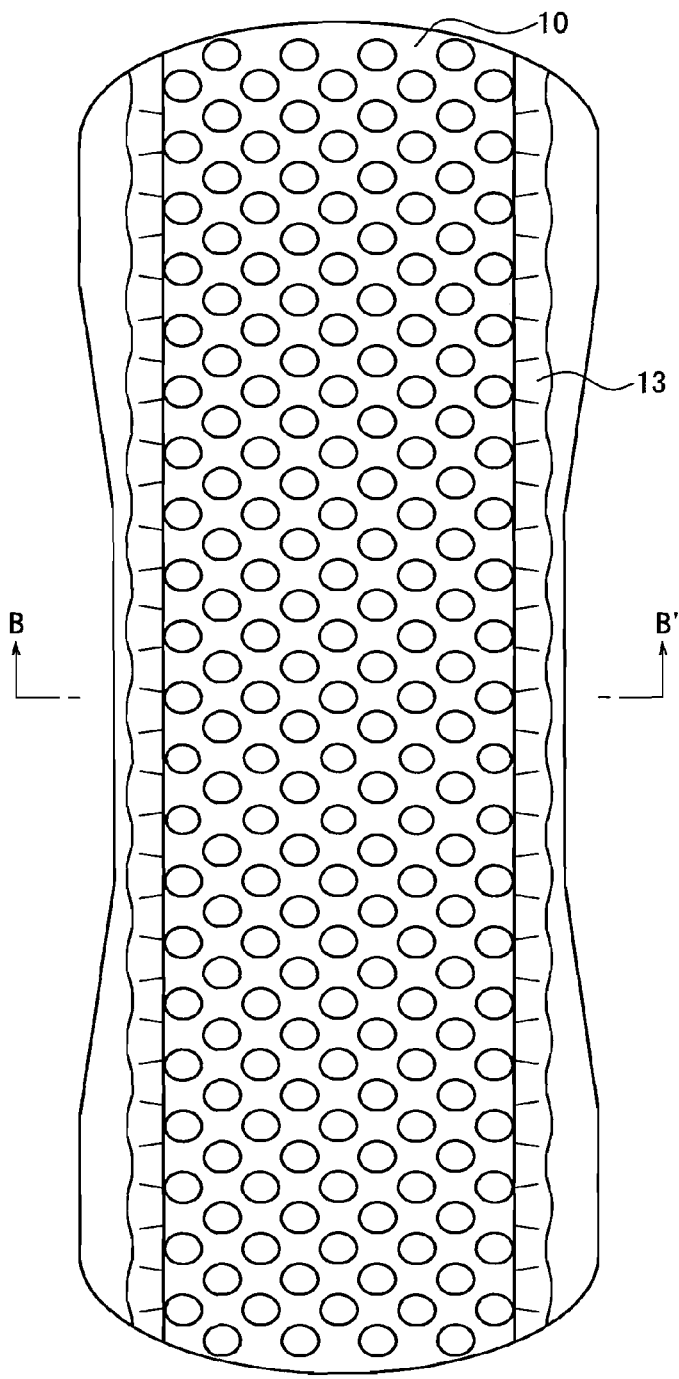
FIG. 3A is a plan view showing the sanitary napkin from the nonwoven fabric side having a surface concavo-convex structure of the present invention.
Figure 3B:
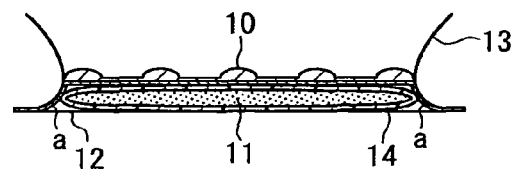
FIG. 3B is a cross-sectional view taken along a line B-B' in FIG. 2B.

FIG. 3 shows a sanitary napkin as an example of a product formed by using the molded member as the surface material. FIG. 3A is a plan view showing the product from the nonwoven fabric side having the surface concavo-convex structure of the present invention. FIG. 3B is a cross-sectional view taken along the line B-B' in FIG. 3A.

Numeral 10 denotes a surface material of the molded member as shown in FIG. 2, which is a liquid-permeable surface covering that passes body fluids such as blood. Numeral 11 is a liquid absorbing layer (for example, it is composed of a mixture layer of pulp and polymer absorbent) enveloped with a tissue paper 14. Further, a liquid impermeable back sheet 12 is arranged on the rear side so as to prevent the absorbed body fluids from leaking outside. Further, water-repelling side sheets (it is called also "side gathers") 13 are provided at both sides of the water-absorbing article for preventing leakage of the absorbed liquid such as the body fluids. Though not shown in the attached drawings, each of the members is heat bonded at appropriate sites by use of a hot melt adhesive or the like so that they will not drop out. In FIG. 3B, at the both lateral ends of the molded member 10 (shown with the sign 'a'), only the both lateral ends of the molded member in FIG. 2B are composed of the web layer 6 alone on which the nonwoven fabric 5 having the surface concavo-convex structure is not laminated.

The molded member shown in FIG. 2 can be used favorably also as the surface material of a disposable diaper similarly to the case of the sanitary napkin as shown in FIG. 3, although the diaper is not shown in any drawings.

Hereinafter, the present invention will be described in detail with reference to EXAMPLES, though the present invention is not limited to the EXAMPLES.

<Nonwoven Fabric Strength>

The strength of the nonwoven fabric is calculated in compliance with the tensile test defined in JIS L1906 (revised on Feb. 20, 2000) by using "Autograph AG500D (trade name)" manufacture by SHIMADZU. The sample for measuring the strength is prepared by cutting a nonwoven fabric to be 150 mm in the direction that the fibers are aligned (MD direction) and 50 mm in the crossing direction (CD direction). The strength was measured at a tensile rate of 100 mm/min. and a holding length of 100 mm.

<Bulkiness>

The weight per unit of the sample (weight per square meter; in fact, a sample weight of 100×100 mm was measured and the value was converted) was measured (w), and the thickness of the sample was measured (t) under the condition of loading of 2 gf/cm² (196 Pa) and measurement rate of 2 mm/sec. by using "Digi-Thickness Tester" (trade name) manufactured by TOYO SEIKI SEISAKUSHO, LTD. The apparent specific volume (v) was calculated by use of the equation below.

$$v = t/w \times 1000 \ (\text{cm}^3/\text{g}) \qquad \text{(Equation)}$$

A higher value of the apparent specific volume (v) indicates that the sample is bulky.

<Maximal Thickness of Nonwoven Fabric Having Surface Concavo-Convex Structure>

The thickness was measured by using "Digi-Thickness Tester (trade name)" manufactured by TOYO SEIKI SEISAKUSHO, LTD under a condition of loading of 2 gf/cm² (196 Pa) and measurement rate of 2 mm/sec. The measurement sample was cut into a 10×10 cm piece and measured at six sites.

<Difference in Height Between Convex Part on Nonwoven Fabric Surface and Adjacent Concave Part)

A nonwoven fabric was sectioned in a direction crossing the planar direction of the nonwoven fabric along a line passing through the center of the convex part, namely, so-called thickness direction. The cross section was subjected to a measurement using a digital microscope (VHX-900) manufactured by KEYENCE so as to measure the thickness at the concave part and the convex part. Measurement was conducted at ten sites so as to obtain the average.

EXAMPLE 1

Heat adhesive concentric sheath-core type conjugated fibers were prepared. For the sheath, a low-melting point component of polyethylene (melting point: 130° C., melt mass flow rate: 16 g/10 min.) was used, and for the core, a high-melting point component of polypropylene (melting point: 160° C., melt mass flow rate: 20 g/10 min.) was used. The sheath and the core were arranged at a ratio of 50/50 in weight, and the fibers had fineness of 2.2 dtex and a cutting length of 51 mm. The fibers were made into a web of 25 g/m² (weight per unit) by a carding method. Interlacing points between the fibers of the web were bonded by passing hot air through the web by use of a 130° C. hot air circulation suction band dryer. Immediately after this bonding, the thus obtained nonwoven fabric was passed at a rate of 8.5 m/min. through a porous roll made of stainless steel and having porosity of 22.7%. The porous roll had circular staggered apertures 5 mm in diameter. In an observation through infrared thermography, the nonwoven fabric temperature at the time of passing through the roll was 70° C., the temperature of the porous roll was 70° C., and the pressure applied to the nonwoven fabric by the porous roll was 0.3 MPa. The obtained concavo-convex nonwoven fabric had a weight per unit of 25 g/m², the maximal thickness was 0.75 mm, and the difference in height between the convex and the concave was 0.5 mm. As the apparent specific volume was 30 cm³/g, the nonwoven fabric was bulky, and the strength was as high as 73 N/5 cm×21 N/5 cm (MD×CD).

EXAMPLE 2

Heat adhesive concentric sheath-core type conjugated fibers were prepared. For the sheath, a low-melting point component of polyethylene (melting point: 130° C., melt mass flow rate: 16 g/10 min.) was used, and for the core, a high-melting point component of polyester (melting point: 250° C., intrinsic viscosity: 0.63) was used. The sheath and the core were arranged at a ratio of 60/40 in weight, and the fibers had fineness of 2.2 dtex and a cutting length of 51 mm. The fibers were made into a web of 25 g/m² (weight per unit) by a carding method. Interlacing points between the fibers of the web were bonded by passing hot air through the web by use of a 130° C. hot air circulation suction band dryer. Immediately after this bonding, the thus obtained nonwoven fabric was passed at a rate of 8.5 m/min. through a porous roll having porosity of 48.6%. The roll had elliptic staggered apertures (10 mm (transverse)×30 mm (longitudinal)). The nonwoven fabric temperature at the time of passing through the roll was 70° C., the temperature of the porous roll was 70° C., and the pressure applied to the nonwoven fabric by the porous roll was 0.3 MPa. The obtained concavo-convex nonwoven fabric had a weight per unit of 25 g/m², the maximal thickness was 1.38 mm, and the difference in height between the convex part and the concave part was 0.87 mm. As the apparent specific volume was 55 cm³/g, the nonwoven fabric was bulky, and the strength was as high as 59 N/5 cm×17 N/5 cm (MD×CD).

COMPARATIVE EXAMPLE 1

Heat adhesive concentric sheath-core type conjugated fibers were prepared. For the sheath, a low-melting point component of polyethylene (melting point: 130° C., melt mass flow rate: 16 g/10 min.) was used, and for the core, a high-melting point component of polypropylene (melting point: 160° C., melt mass flow rate: 20 g/10 min.) was used. The sheath and the core were arranged at a ratio of 50/50 in weight, and the fibers had fineness of 2.2 dtex and a cutting length of 51 mm. The fibers were made into a web of 25 g/m² (weight per unit) by a carding method. The web was pressed at pressure of 1.96 MPa and at a rate of 6 m/min. with upper and lower rolls at 124° C. The rolls were emboss/flat heat compression rolls having rhombus convexes and whose emboss area rate was 23%. The obtained concavo-convex nonwoven fabric had a weight per unit of 25 g/m², the maximal thickness was 0.3 mm, and the difference in height between the convex part and the concave part was 0.2 mm. Though the obtained nonwoven fabric exhibited a strength as high as 55 N/5 cm×24 N/5 cm (MD×CD), the apparent specific volume was 12 cm³/g, namely, the bulkiness was considerably inferior, and the feeling was rigid.

COMPARATIVE EXAMPLE 2

For a plain weave mesh sheet, a net 10 mm in the yarn spacing and 13 g/m² in the basic weight was used. A low-melting point component of polyethylene (melting point: 130° C., melt mass flow rate: 16 g/10 min.) was used and for the core, a high-melting point component of polyester (melting point: 250° C., intrinsic viscosity: 0.63) was used. The sheath and the core were arranged at a ratio of 60/40 in weight to form a heat adhesive concentric sheath-core type conjugated fiber having a fineness of 2.2 dtex and a cutting length of 51 mm. The heat adhesive concentric sheath-core type conjugated fibers were made to a web having a weight per unit of 25 g/m², by a carding method. The web as an upper layer is stacked on the net, to which hot air was applied by using a 130° C. hot air circulation type suction band dryer so as to be integrated. The thus obtained nonwoven fabric had a weight per unit of 35 g/m², and the apparent specific volume was as low as 23 cm³/g. Furthermore, since the hot air does not pass through the regions where the net was integrated, the accumulation of fibers becomes irregular and the bonding between fibers was insufficient, and the strength of the obtained nonwoven fabric was as low as 22.5 N/5 cm.

INDUSTRIAL APPLICABILITY

A nonwoven fabric and a molded member of the present invention, having bulky hill parts (convexes) and the plain parts (concaves) are intermingled on the nonwoven fabric surface, are bulky and have an excellent softness. Due to the effect of scraping (wiping) soils and the favorable feeling/touch, they can be used preferably for a baby wipe and a wiping cloth. Furthermore, due to the excellent bulkiness and softness, they can be used for absorbing articles such as a top sheet or a second sheet of a disposable diaper or a sanitary napkin.

EXPLANATION OF LETTERS AND NUMERALS 1 planar element
2 aperture
3 convex part (hill part)
4 concave part (plain part)
5 nonwoven fabric having surface concavo-convex structure
6 web layer of polyester fiber
7 hot melt adhesive
10 surface material of molded member as shown in FIG. 2
11 liquid absorbing layer
12 liquid impermeable back sheet
13 side sheet
14 tissue paper

The invention claimed is:

1. A nonwoven fabric having a surface concavo-convex structure,
which is formed by pressing a planar element having a plurality of apertures against at least one surface of a nonwoven fabric that has been treated by passing hot air through a web comprising heat adhesive fibers so as to heat-bond the heat adhesive fibers in the nonwoven fabric at interlacing points between the heat adhesive fibers,
wherein the nonwoven fabric is heat-bonded entirely across the heat adhesive fibers at the interlacing points between the heat adhesive fibers,
the pressing process is performed in a state in which the nonwoven fabric is heated in a degree that does not further promote the heat bonding,
bulky hill parts forming convex parts in the surface concavo-convex structure and less bulky plain parts forming concave parts in the surface concavo-convex structure are intermingled with each other on the surface of the nonwoven fabric including the heat adhesive fibers,
each of the bulky hill parts forming the convex parts is formed at a position corresponding to one of the plurality of the apertures of the planar element, and each of the less bulky plain parts forming the concave parts is formed at a position corresponding to one part of a non-aperture area of the planar element, when the planar element is pressed against the nonwoven fabric,
the concave parts in a shape of a plain at the positions corresponding to the non-aperture area of the planar element surround the convex parts and form a network linking the concave parts with each other via the plain of the nonwoven fabric,
the bulky hill parts of the nonwoven fabric are formed so that a bulkiness of the bulky hill parts is not suppressed toward a space above the bulky hill parts, while the heat adhesive fibers in the bulky hill parts are heat-bonded at the interlacing points between the heat adhesive fibers in the bulky hill parts,
the heat adhesive fibers are heat adhesive conjugated fibers,
the heat adhesive conjugate fibers in the web are heat adhesive conjugate fibers that have been cut, and
wherein the nonwoven fabric has an apparent specific volume in a range from 20 to 70 cm³/g.

2. The nonwoven fabric according to claim 1,
wherein the planar element having the plurality of the apertures is a cylindrical roll that is used as a rotational roll through which the nonwoven fabric is passed while being pressed against the rotational roll.

3. The nonwoven fabric according to claim 1, wherein the web is a laminate.

4. The nonwoven fabric according to claim 1, having a weight per unit in a range from 15 to 60 g/m² and a maximal thickness in a range from 0.2 to 5 mm.

5. The nonwoven fabric according to claim 1, wherein the difference in height between the convex part and the concave part adjacent to the convex part on at least one surface is in a range from 0.1 to 4.5 mm.

6. A molded member comprising: the nonwoven fabric according to claim 1; and an additional layer, wherein the nonwoven fabric and the additional layer are integrated with each other.

7. A product comprising the nonwoven fabric according to claim 1.

8. A wiping cloth comprising the nonwoven fabric according to claim 1.

9. A product comprising the molded member according to claim 6.

10. A wiping cloth comprising the molded member according to claim 6.

* * * * *